United States Patent [19]

Deeg et al.

[11] Patent Number: 5,378,638
[45] Date of Patent: Jan. 3, 1995

[54] ANALYSIS ELEMENT AND PROCESS FOR ITS MANUFACTURE

[75] Inventors: Rolf Deeg, Bernried; Eberhard Maurer, Weilheim; Sigmar Klose, Berg; Bernhard Köpfer, Tutzing; Reiner Babiel, Eberfing, all of Germany

[73] Assignee: Boehringer Mannheim GmbH, Mannheim, Germany

[21] Appl. No.: 63,069

[22] Filed: May 20, 1993

Related U.S. Application Data

[63] Continuation of Ser. No. 736,919, Jul. 25, 1991, abandoned.

[30] Foreign Application Priority Data

Aug. 2, 1990 [DE] Germany .............................. 4024544

[51] Int. Cl.$^6$ .................. G01N 33/543; G01N 33/558
[52] U.S. Cl. ........................................ 436/518; 422/57;
422/58; 422/61; 427/258; 427/286; 427/338;
427/414; 435/7.5; 435/291; 435/805; 435/810;
435/969; 435/970; 436/164; 436/514; 436/531;
436/805; 436/807; 436/809; 436/810
[58] Field of Search ............................ 422/56–58,
422/61; 427/2, 258, 286, 338, 414; 435/174,
175, 7.5, 180–182, 287, 288, 291, 805, 808, 810,
969, 970; 436/164, 169, 170, 514, 518, 531, 805,
807, –810

[56] References Cited

U.S. PATENT DOCUMENTS

| | | | |
|---|---|---|---|
| 4,216,245 | 8/1980 | Johnson | 422/57 |
| 4,496,654 | 1/1985 | Katz et al. | 436/530 |
| 4,591,570 | 5/1986 | Chang | 435/300 |
| 4,853,325 | 8/1989 | Vodian et al. | 422/58 |
| 4,861,711 | 8/1989 | Friesen et al. | 422/56 |
| 4,870,007 | 9/1989 | Smith-Lewis | 436/531 |
| 4,877,745 | 10/1989 | Hayes et al. | 422/56 |
| 4,988,627 | 1/1991 | Smith-Lewis | 422/58 |
| 5,061,640 | 10/1991 | Tischer et al. | 436/524 |
| 5,089,420 | 2/1992 | Albarella et al. | 422/56 |

FOREIGN PATENT DOCUMENTS

| | | |
|---|---|---|
| 1101771 | 5/1981 | Canada . |
| 1187786 | 5/1985 | Canada . |
| 61167 | 9/1982 | European Pat. Off. . |
| 0119573 | 9/1984 | European Pat. Off. . |
| 192428 | 8/1986 | European Pat. Off. . |
| 212642 | 3/1987 | European Pat. Off. . |
| 299428 | 1/1989 | European Pat. Off. . |
| 0344578 | 12/1989 | European Pat. Off. . |
| 0408078 | 1/1991 | European Pat. Off. . |
| 2355290 | 1/1978 | France . |
| 3346795 | 7/1985 | Germany . |
| 8404171 | 10/1984 | WIPO . |

*Primary Examiner*—Toni R. Scheiner
*Assistant Examiner*—Christopher L. Chin
*Attorney, Agent, or Firm*—Nikaido, Marmelstein, Murray & Oram

[57] ABSTRACT

An analysis element for the determination of an analyte in a liquid sample, especially for medicinal uses. A carrier layer (2) contains, in a reagent domain (4), a reagent applied in a defined pattern by an ink-jet process. The pattern comprises several sets (A, B, C) of compartments (11–20), the compartments (e.g. 11, 13, 15, 17, 19) of the same set (e.g. A) having the same chemical composition, the compartments (11, 13, 15, 17, 19 or 12, 16, 20) of different sets (A or B) containing different reagents and the compartments of different sets being arranged in alteration so that the compartments containing different reagents are close together but nevertheless spatially separated.

11 Claims, 3 Drawing Sheets

ANALYSIS ELEMENT AND PROCESS FOR ITS MANUFACTURE

This application is a continuation of application Ser. No. 07/736,919 filed Jul. 25, 1991, now abandoned.

BACKGROUND OF THE INVENTION

1. Field of the Invention

The invention relates to an analysis element for the determination of an analyte in a liquid sample, said analysis element having a carrier layer which contains, in a reagent domain, a reagent applied in a defined pattern by an ink-jet process.

2. Description of the Prior Art

Analytical examinations on liquid samples, especially body fluids such as blood or urine, are frequently carried out with the aid of analysis elements, which are also referred to as: solid state analysis elements. They are available in a variety of external forms, especially as extended test strips and as small square sheets. In every case, they have one or more test layers which contain the reagents required for the analysis. The test layers are brought into contact with the liquid sample and the reaction of the analyte with the reagents produces a physically measurable detection signal, especially a colour change which can be measured visually or photometrically. Examples of other known detection signals are optical fluorescence, luminescence and, in the case of electrochemical analysis elements, voltage or current signals.

Particular importance has recently been attached to analysis elements which work on the basis of a specific binding reaction between two bioreactive binding partners. Specific binding reactions in this sense are especially immunological interactions, i.e. interactions between antigens or haptens on the one hand and antibodies on the other. However, it is also possible to use other specific bioreactive interactions such as lectin-sugar, an interaction between an active substance and a receptor, the specific binding between biotin and streptavidin or certain enzyme-substrate binding reactions, e.g. inhibitors or suicide substrates.

The reagents are generally incorporated in the test layers, the normal case being either that a porous support matrix (e.g. made of paper or plastic) is impregnated with reagent or that, in a layering process, a reagent film is produced which contains the reagents dissolved or dispersed in a film former. As a rule, in the manufacture of analysis elements, different mutually incompatible reagents have to be accommodated so as to be spatially separated. This is conventionally achieved by joining together (e.g. by welding or adhesive bonding) individual preprepared reagent support elements. These processes are very expensive, often cause production defects and only allow limited miniaturization.

It has recently been proposed to use the ink-jet technology originally developed for computer printers (ink-jet printers) in the manufacture of analysis elements. In this context, reference may be made to EP-A-119573 and EP-A-268237 (U.S. Pat. No. 4,877,745). Both patent specifications contain more detailed explanations of the previously known state of the art, including ink-jet technology in particular, to which reference is made here.

The distinguishing feature of the ink-jet technique is that very small quanta (partial amounts) of a liquid can be applied as drops to a carrier layer with high precision, the precision relating both to the exact positioning of the dot produced by the drop of reagent on the reagent domain and to the reagent volume. The drops can be ejected successively at high frequency.

Reagent patterns produced by an ink-jet process differ unambiguously from the patterns obtainable by other printing techniques. In particular, comparably fine reagent dots cannot be produced in any other way with similar uniformity.

A special variant of the ink-jet technique, which is also particularly suitable for the invention, is the drop-on-demand technique, where individual drops of liquid can be produced at any desired point in time and applied to a carrier layer. In connection with the metering of biochemical analytical liquids, especially reagents, only the technique described in the mentioned patent specifications has so far been used, where the volume of a jet chamber is compressed every time a drop is to be ejected. A piezoelectric change in the volume of the jet chamber is utilized in particular here. In U.S. patent application entitled "Method and device for the metered application of a biochemical analytical liquid to a target" U.S. patent application Ser. No. 07/735,580 filed of even date herewith by the present invention now abandoned, the use of bubble-jet technology for the application of liquid reagents to a reagent domain is described which is also suitable for the present invention, and such copending application is hereby incorporated by reference. The term ink-jet is to be understood hereafter as encompassing both said procedures.

The ink-jet technique makes it possible to apply reagents to a reagent domain of an analysis element, with high precision and uniformity, as a reagent layer of exceptionally low thickness. Said patent specifications also mention the possibility of applying the reagent to the carrier layer in a particular pattern, e.g. in order to allow a direct comparison between a subdomain coated with reagent and a reagent-free subdomain, or in order to make the result of the analysis more clearly visible, because the formation of colour appears for example in the form of a plus or minus sign.

De-A-27 27 347 and De-C-27 29 233 have disclosed an alternating arrangement of dots (especially spots) of different reagents which are applied by a screen printing technique. However, this process is very expensive. Moreover, the amounts of reagent applied cannot be metered accurately. The dots are relatively large and can only be miniaturized to a limited extent. Many reagents cannot be processed to pastes suitable for screen printing without being damaged or having their properties changed, so this process, which has been know for a long time, has not achieved any practical significance.

SUMMARY OF THE INVENTION

According to the invention, an analysis element of the type indicated at the outset is characterized in that the pattern applied to the reagent domain comprises several sets of compartments, the compartments of the same set having the same chemical composition, the compartments of different sets containing different regents and the compartments of different sets being arranged in alteration so that the compartments containing different reagents are close together but nevertheless spatially separated. The average distance between the outer limits of the compartments of different sets is typically less than 1 mm and preferably less than 0.5 mm. The combination of the measures according to the invention is also denoted as "microcompartmentalization" hereafter.

The term "compartment" denotes a delimited subdomain. A compartment can consist of one dot or several mutually overlapping dots. The compartments which contain different reagents (and thus belong to different sets of compartments in the reagent domain) are at least in some cases spatially separated from one another in that they are arranged next to one another (although not necessarily in the same plane) in the reagent domain, the compartments containing different reagents being alternate, i.e. compartments of different sets being alternately adjacent. For practical reasons, it is convenient to have regular alteration where, for example, the compartments of three sets A, B and C are present in a cyclically repeating pattern A, B, C, A, B, C, A, B etc. In exceptional cases, however, it may also be convenient to have an alternating pattern without cyclic repetition.

The compartments can also be arranged on top of one another in some cases. A spatial separation of the compartments in the direction perpendicular to their planar dimension (vertical compartmentalization) is possible here if an isolating intermediate layer consisting of a soluble inert isolating substance (e.g. an inert protein or film former) is applied.

In the process according to the invention, the volume of a quantum of liquid reagent ejected from an ink-jet head is typically between 20 and 2000 picoliters and preferably between 100 and 800 picoliters. The area of the dot produced by such a quantity on the carrier layer is greatly dependent on the properties of the liquid reagent and the carrier layer. It is approximately between 500 $\mu m^2$ and 0.2 $mm^2$ and preferably between 3000 $\mu m^2$ and 0.1 $mm^2$. The quantities of liquid reagent are typically ejected at a frequency of more than 1000 $sec^{-1}$ and preferably of between 2000 and 20,000 $sec^{-1}$.

Depending on the test procedure for which an analysis element according to the invention is set up, the compartments can contain both elutable reagents and reagents which are solid-phase-bound on the carrier layer, it being possible for the reagent domain to contain exclusively compartments with elutable reagents ("elutable compartments"), exclusively compartments with reagents bound to the solid phase ("fixed compartments") or a mixture of elutable and fixed compartments, the following advantages, inter alia, thereby being achieved according to the invention.

The reagents in elutable compartments are rapidly dissolved by the liquid sample and mixed together. By the addition of solubility-modifying constituents to the liquid reagent, it is possible to modify the solubility properties of the individual reagents in the compartments of different sets in order to permit a particular reaction sequence. Also, by varying the layer thickness of different compartments, it is possible to influence the dissolution properties so as to permit a flexible adaptation to the reaction sequence in question. Examples of reagents which are used predominantly in elutable form are enzymes, substrates, coenzymes and indicator components, especially colour reagents.

Reagents bound to the solid phase can be bound both adsorptively and covalently. IN the case of adsorptive binding, it is advantageous if (in contrast to the screen printing technique) water-based coating solutions can be used which do not contain any hydrophobic additives interfering with the adsorptive binding. Reagents which are to be bound to the fixed phase on the carrier layer can be precisely located, it being possible in particular to determine the diffusion distances to other reagents (bound to the fixed phase or elutable) in other sets of compartments in accordance with the requirements of each individual case.

In general, the invention permits very short diffusion distances between the reagents contained in different sets of compartments, and hence relatively short reaction times and thorough mixing of the reagents without special additional measures.

Within the framework of the present invention, it has been established that the microcompartmentalization made possible by ink-jet technology opens up completely new test procedures.

As already mentioned, the invention is of particular significance for homogeneous and heterogeneous methods of determination base on the specific binding capacity of two bioreactive binding partners. In this case, at least one set of compartments contains a first binding partner capable of binding specifically to a second binding partner, which can be contained in the liquid sample or be a reagent. Often at least one of the binding partners is solid-phase-bound on the carrier layer.

In the preparation of fixed compartments, it is frequently advantageous if the binding partner which is to be fixed is applied in a concentration (per unit area) which is lower than the binding capacity (per unit area) of the surface to which it is fixed. This makes it possible to avoid the additional process steps, especially removal of the excess by washing, which are otherwise necessary in the fixing of reagents to carriers.

BRIEF DESCRIPTION OF THE DRAWINGS

The invention is illustrated in greater detail below with the aid of Examples which are represented schematically in the Figures.

DESCRIPTION OF THE PREFERRED EMBODIMENT

Figure 1:
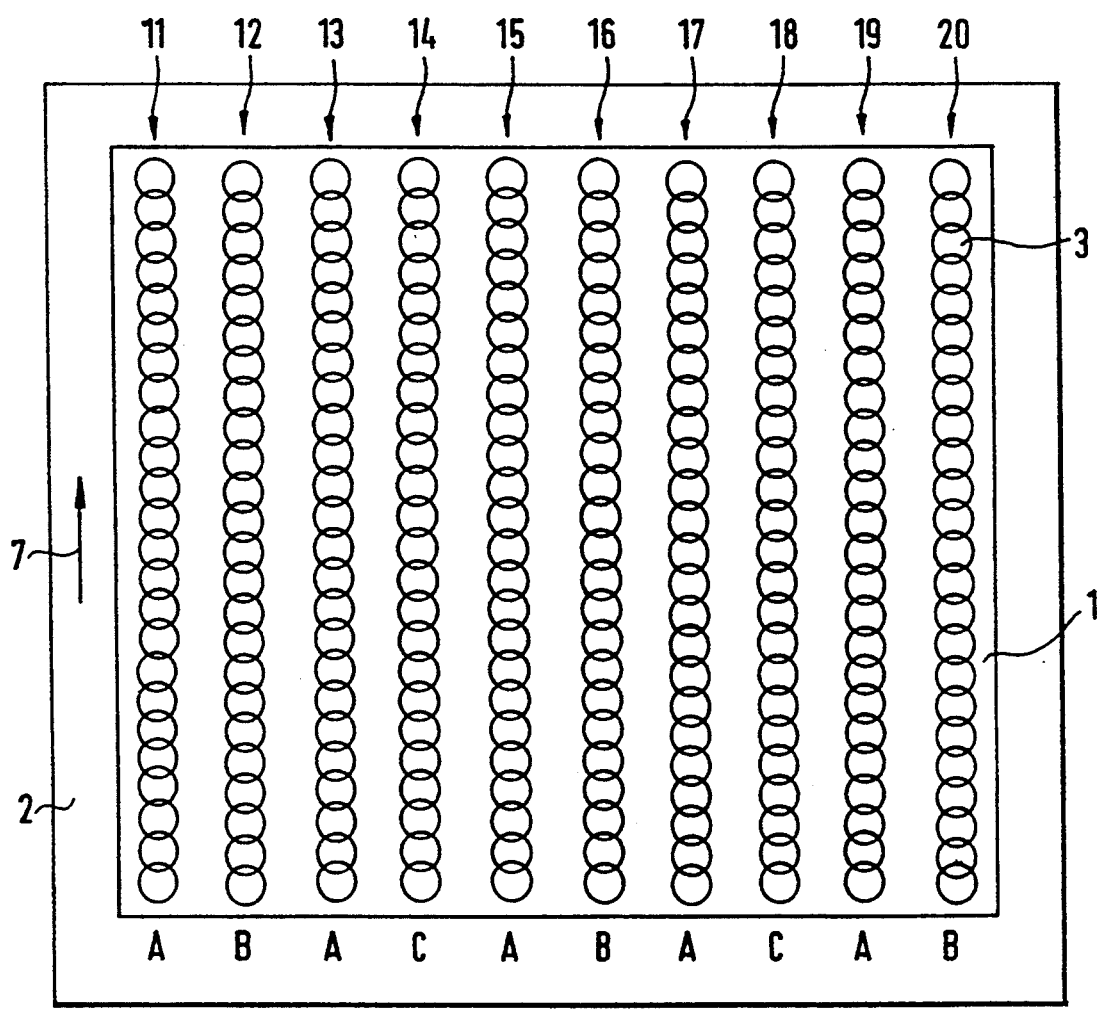
FIG. 1 is an overhead view showing part of an analysis element according to the invention.

The reagent domain 1 shown in FIG. 1 contains ten rows of reagent compartments 11 to 20, which are applied next to one another on a carrier layer 2. Each of the compartments consists of a large number of dots 3, which are applied to the reagent domain 1 with an ink-jet printing head. The procedure is preferably as follows:

The carrier layer 2 used is a plastic film (made especially of polystyrene) which has first been irradiated with gamma rays under standardized conditions (EP-B1-0 061 167). It is then positioned under an ink-jet printing head which can make precise movements relative to the carrier layer 2, and is printed with the dots 3.

A special technique is used to achieve a uniform application of the reagent, covering continuously the area of each of the compartments 11 to 20. In a first process step, only every other dot within a compartment is applied, the quanta of liquid reagent applied in this process step thus forming spatially separated dots. After the reagent has been dried (ca 60 sec at room temperature), quanta of liquid reagent are applied in a second step, at a different time, to the spaces between the dots produced in the first step, so as to form a continuous compartment. This procedure is particularly advantageous when an aqueous liquid reagent has to be applied to a relatively hydrophobic surface of the carrier layer 2. Frequently, however, it is also possible to avoid the need for the described two-step procedure by influencing the surface properties of the carrier layer material or by modifying the composition of the liquid reagent.

In the case illustrated, the compartments 11 to 20 are identical in their external form and in their physical structure (which is preferred although not necessary), but differ in respect of their chemical composition. They can be divided into sets, which are denoted by the letters A, B and C in FIG. 1. The compartments within a set contain the same reagent composition, while the compartments of different sets differ in respect of their reagent composition, the compartments of different sets being arranged alternately so that the compartments containing different reagents are close together but nevertheless spatially separated.

In the case illustrated, every other compartment is to be assigned to set A. The number of compartments in each of sets B and C is only half as large and they are placed alternately in the gaps between the compartments of set A.

The dimensions of the compartments and the distances between them are exceptionally small. In one case evaluated in practice, the distance between the dots within one compartment was only about 0.14 mm, the centre-to-centre distance between the compartments was about 0.26 mm in this example and the average distance between the limits of the compartments was less than 0.15 mm.

The compartments of different sets can advantageously be produced in a single pass with the aid of a multichannel printing head or a printer equipped with several printing heads. Printers of these types, working by the ink-jet process, were developed for colour printing. The pattern of compartments shown in FIG. 1 can be produced for example by using linearly arranged jets of a multichannel printing head for the different compartments and moving the printing head over the carrier layer 2 in the direction perpendicular to the linear arrangement of jets (arrow 7). This makes it possible to manufacture the analysis elements according to the invention in a precise and at the same time economic manner.

The movement of the printing head relative to the carrier layer can be effected with the constructions conventionally used for ink-jet printers. Within the framework of the invention, it is advantageous to operate the printing head unidirectionally in order to permit particularly precise positioning of the dots.

Figure 2:
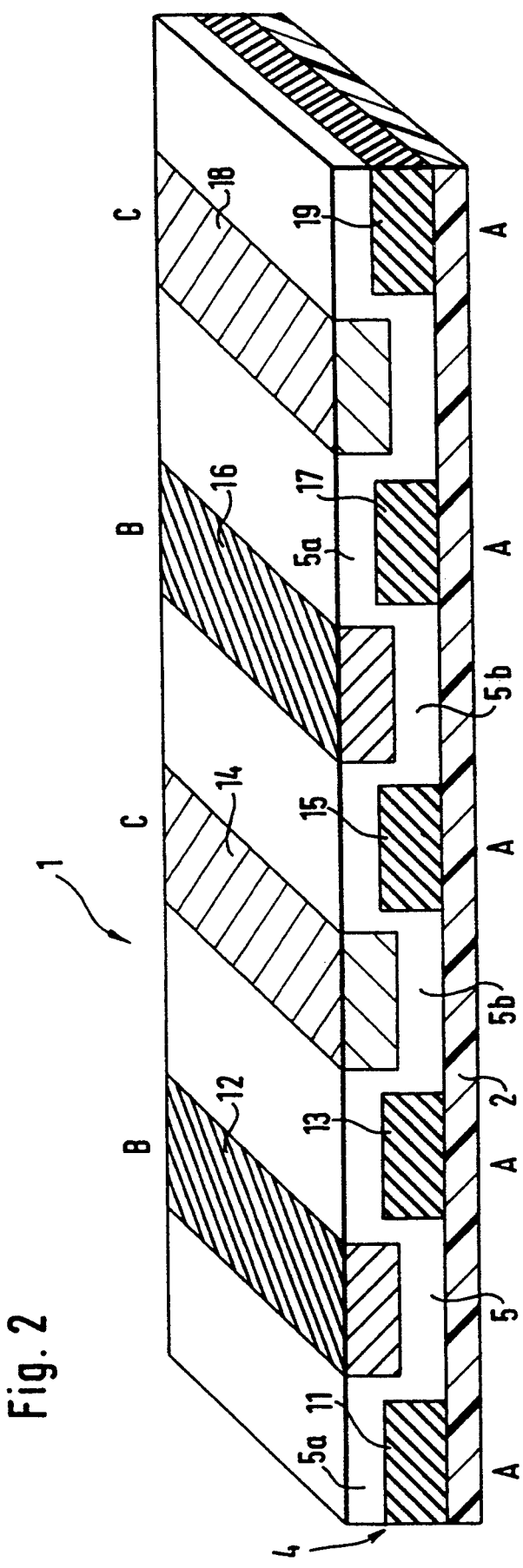
FIG. 2 is a basic diagram in perspective of the reagent domain of an immunological analysis element.

FIG. 2 is a very schematic basic diagram showing the layer structure in the reagent domain of an analysis element for immunological determinations.

Three sets of compartments—A (compartments 11, 13, 15, 17 and 19), B(compartments 12 and 16) and C (compartments 14 and 18)—are again shown on the carrier layer 2. The three-dimensional representation reveals another preferred measure, namely that the individual compartments are separated from one another by a separating layer 5 containing an inert water-soluble substance, in particular a water-soluble protein such as bovine serum albumin. The separating layer is applied by a procedure in which, after application of the compartments belonging to set A, the BSA is applied in several passes from a printing head, not only the jets directed at compartments 11 to 20 but also intermediate jets of the pressure head being activated in order to form the continuous BSA layer.

The compartments 11 to 19 and the BSA separating layer 5 together form a reagent layer 4 on the carrier layer 2. In practice, the shape of the compartments is not as uniform and rectangular as shown in FIG. 2. It is a characteristic of the invention, however, that the compartments are spatially separated from one another, at least some of the compartments belonging to different sets being arranged side by side on the carrier layer 2 (horizontal compartimentalization).

In a preferred embodiment, the compartments of set A contain a first binding partner fixed to the support, Bp(b) (binding partner, bound). It is advantageous here if the compartments containing the first binding partner are covered with a protective layer 5a of an inert protecting substance. A soluble protein which does not react with the other test components is particularly suitable. It is often mixed with a sugar compound. The protective layer ensures the required storage stability of the binding partner fixed to the support, BP(b).

At least one other set of compartments B or C contains a second, free binding partner, Bp(f) (binding partner, free), capable of binding specifically to Bp(b), "free" meaning that it can easily be dissolved by the liquid sample. Bp(f) is preferably labelled by a method conventionally used in immunology (for example by conjugation with a labelling substance M, e.g. an enzyme or a fluorescent marker). In this case, as well as with other elutable compartments, it is advantageous if a blocking portion 5b, covering the carrier layer 2, is arranged under the compartments 12, 16. The blocking portion 5b is also conveniently based on a soluble inert protein and serves to prevent unspecific binding of the elutable reagent (Bp(s) here) to the carrier layer 2 and hence to improve the elutability of Bp(f).

In the embodiment shown in FIG. 2, the protective portions 5a, which cover the compartments 11, 13, 15, 17 and 19, and the blocking portions 5b, which are arranged underneath the compartments 12, 14, 16 and 18, run into one another and together form the separating layer 5. This is particularly advantageous, although not necessary. Provision could also be made for separated protective and blocking portions.

Further details depend on the immunological test principle on which the analysis element works. For example, if the analyte is an antigen Ag(s) (antigen, sample, Bp(f) can be an antigen Ag(f) analogous to Ag(s) when using a competitive test principle. Bp(b) in this case is an antibody Ab(b) (antibody bound) capable of binding specifically to Ag(f). The analytical procedure here is based on the fact that Ag(s) competes with Ag(f) for binding sites on Ab(b), the amount of Ag(f) bound to Ab(b), which is detectable due to the labelling of Ag(f), being a measure of the concentration of the analyte. Via the labelling, the concentration of Ag(f) can be determined preferably in the bound phase, but in principle also in the free phase.

According to another immunological reaction principle ("one-step sandwich"), the compartments B or C (again for determining an antigen Ag(s) can contain an antibody Ab(f) capable of binding specifically to Ag(s). In this case, the set of compartments A contains an antibody Ab(b) fixed to the support, which is capable of binding specifically to Ag(s) via a second epitope. The test method is based in this case on the fact that Ag(s) promotes binding between Ab(b) and Ab(f).

If an antibody is to be determined rather than an antigen, the bound and free immunological reaction components have to be respectively exchanged in the compartments (antigen for antibody and vice-versa).

These and other immunological test principles suitable for the invention have been known for a long time. Reference may be made, for example, to U.S. Pat. No. 4,861,711 and numerous other publications describing the application of heterogeneous immunological reactions to analysis elements in different variants.

Table 1 shows the arrangement of the sets of compartments for the aforementioned reaction principles as well as a few others:

TABLE 1

|  | Bp(s) | Bp(b) in A | Bp(f) in B and/or C |
|---|---|---|---|
| sandwich | Ag | Ab | Ab-M |
|  | Ab | Ag | Ag-M |
| competitive | Ag | Ab | Ag-M |
|  | Ab | Ag | Ab-M | compared with the known immunochemical analysis elements, the invention achieves a significant simplification of the manufacture and structure of an imunological analysis element by applying the ink-jet technique to produce compartments of different immunological reaction components arranged in alternation and spatially separated, but nevertheless close together.

It is found that the soluble binding partner contained in a first set of compartments is very rapidly dissolved by the sample, so the reaction of this binding partner with the analyte begins immediately after contact with the sample. At the same time, the entire sample is in contact with the binding partner fixed to the support. The microcompartmentalization of the reagents enables the binding reactions in question to proceed rapidly and homogeneously with a very small amount of sample and reagent and a high reaction rate. Here the reaction with the free binding partner preferably takes place first, while the reaction with the solid-phase-bound binding partner proceeds substantially more slowly as a heterogeneous reaction and, in practice, does not set in to a significant extent until after the binding reaction of Bp(f) has taken place.

According to a preferred embodiment of the invention, at least three different sets of compartments are applied to the reagent domain of an analysis element: a first binding partner Bp(b), fixed to the support, in Set A, a second binding partner Bp(f)2, which is free and carries a marker, in set C and a third binding partner Bp(f)1, which is also free, in Set B. Here the third binding partner Bp(f)1 is capable of binding both to the first binding partner Bp(b) and to the second binding partner Bp(f)2 with different specificities. Preferably, the first binding partner Bp(b) is the same for different analysis elements, while the two free binding partners are selected according to the analyte (parameter) to be determined and the chosen method. The first binding partner preferably contains streptavidin (SA) or avidin and the third binding partner preferably contains biotin (b). The biotin is conjugated with an antigen or antibody, depending on the test procedure, to give Ag-B or Ab-B.

Table 2 shows the arrangement of the sets of compartments for two different test principles, it being assumed in each case that an antigen is to be determined in the sample. If an antibody is to be determined, antigen and antibody have to be exchanged.

TABLE 2

| To determine an Ag | Bp(b) | Bp(f)1 | Bp(f)2 |
|---|---|---|---|
| competitive (a) | SA | B-Ag | Ab-M |
| (b) | SA | B-Ab | Ag-M |
| sandwich | SA | B-Ab | Ab-M |

With each of these principles, after dissolution of the free binding partners, Bp(f)1 binds to Bp(b) via the avidin-biotin bond.

In the competitive test of type (a), the binding of Ab-M to B-Ag is determined by competition with the sample antigen Ag(s). In the competitive test of type (b), Ag(s) competes with Ag-M for binding sites on the antibody of B-Ab. In the sandwich test, the sample antigen again promotes binding between the antibody of B-Ab and the antibody of Ab-M.

In this embodiment, the streptavidin (or avidin), which is fixed to the carrier, and the biotin, which is covalently bound to other reagents, form a so-called capturing system. The use of a capturing system makes it possible easily to bind different reagent components to a fixed phase which has been pretreated homogeneously (with a single binding component, in this case streptavidin). Within the framework of the present invention, this can furthermore be done in a precisely locatable form. On the other hand, it is also possible to apply soluble compartments (non-biotinylated reagents) to a carrier layer which has been pretreated homogeneously, for example with streptavidin, without their solubility properties being substantially affected. Further details can be found in EP-A-0 269 092 and EP-A-0 344 578.

Figure 3:
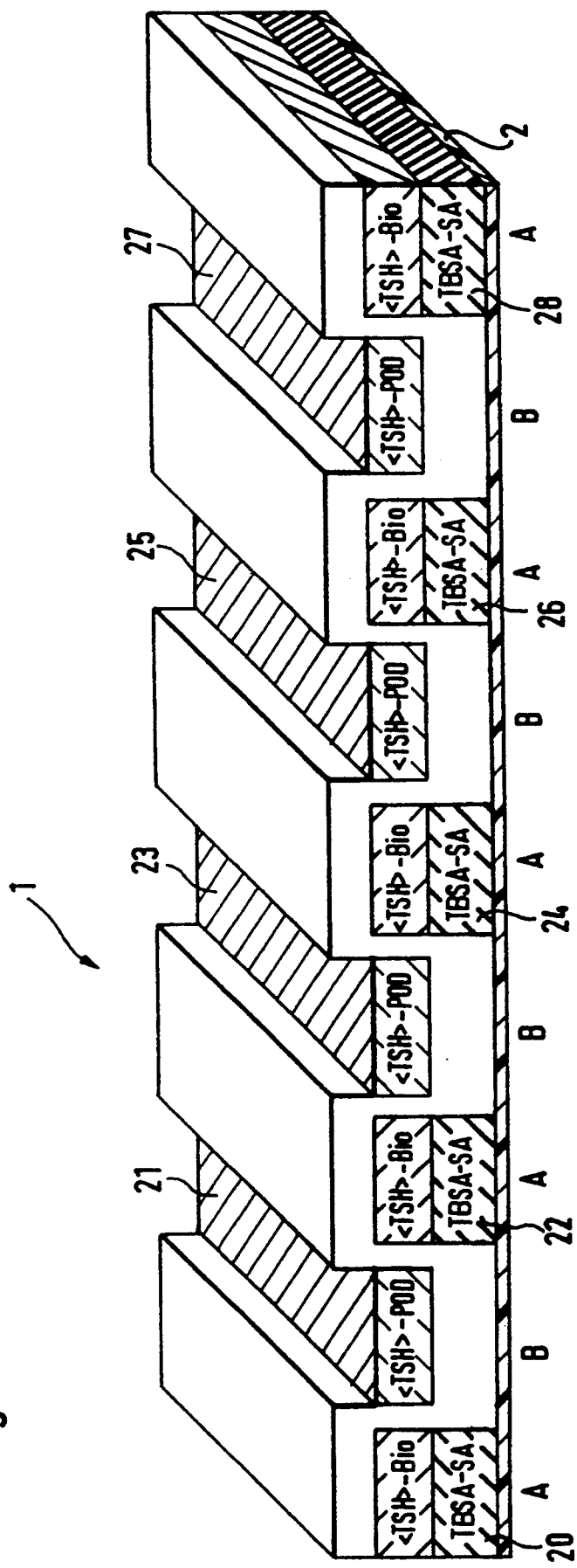
FIG. 3 shows an alternative embodiment of the reagent domain of an immunological analysis element.

FIG. 3 shows an alternative embodiment of a test carrier with three sets of compartments containing three different binding partners. The test composition is essentially the same as that of the previous embodiment, except that in this case the third binding partner is coated directly on the first binding partner and is thus bound to the latter. The two bound binding partners are therefore denoted as Bp(b)1 and Bp(b)2. They are located in double compartments 20, 22, 24, 26, 28 of set A. The second binding partner is a free binding partner Bp(f) in the compartments 21, 23, 25, 27 of set B.

The following Examples serve to illustrate the invention further. Unless stated otherwise, all data in % denote percentages by weight.

EXAMPLE 1 an Epsom SQ-2550 ink-jet printer was used to apply the compartments. In place of the ink reservoir, a separate reagent reservoir, containing the particular reagent solution to be metered, was connected to the system of tubes leading to the printing head. The printer was run in the graphics mode (individual jet drive) via a personal computer.

The support material used was a 0.1 mm thick DIN A4 blank made of polystyrene film. The film was subjected to standardized gamma irradiation before use.

Characteristics of the printing head:
24 jets arranged in two rows (offset by half a line)
drop diameter: ca. 90 μm
smallest meterable volume (1 drop): ca. 420 picoliters
print density per printing step: 180×180 dots/inch2.

The compartments are applied by the procedure described in connection with FIG. 1. Each of the reagent compartments consists of 24 individual drops of ca. 400 picoliters each. The dimensions of a compartment are ca. 3.2 mm high by ca. 0.06 to 0.08 mm wide. The centre-to-centre distance between the compartments is ca. 0.26 mm.

The separating layer based on bovine serum albumin ("BSA separating layer" hereafter) was applied with a total of four print runs, the distance between dots being 0.14 mm horizontally and 0.14 mm vertically.

The arrangement of the compartments in the reagent domain corresponded to FIG. 2. The following solutions were used for the individual sets of compartments.

a) Set of compartments A: Bp(b) (namely SA): SA fixed to the support

| Coating solution: | 0.25 mg/ml | TBSA-SA |
|---|---|---|
| | 40 Mm | sodium phosphate buffer (NaPB) pH 7.4 |
| | 5 vol % | isopropanol |

TBSA-SA denotes thermo bovine serum albumin-streptavidin according to EP-A-0 269 092 and EP-A-0 344 578. This compound is especially suitable for the adsorptive fixing of streptavidin to the support. The amount of TBSA-SA applied per unit area was marginally less than the adsorptive binding capacity of the support film, thereby avoiding additional process steps to ensure quantitative and stable binding to the fixed phase.

b) Protective layer 5: BSA separating layer

| Coating solution: | 0.6% | bovine serum albumin (BSA) |
|---|---|---|
| | 4.0% | sucrose |
| | 1.8% | sodium chloride (NaCl) |
| | 5.0 vol % | isopropanol | c) Set of compartments B: Bp(f)1 (namely B-Ag): Elutable conjugate consisting of T3 and biotin (T3-biotin), prepared by coupling biotin with N-butoxycarbonyl-triiodothyronine (T3) via pentamethylenediamine (Eur. J. Biochem, 131 (1980, 333–338)).

| Coating solution: | 200 ng/ml | T3-biotin |
|---|---|---|
| | 120 mM | sodium barbiturate |
| | 21.8 mM | NaPB pH 8.35 |
| | 0.04% | 8-anilinonaphthalene-1-sulphonic acid (ANS) |
| | 0.02% | 4-aminoantipyrine |
| | 0.01% | Merthiolate |
| | 0.25% | bovine IgG (B-IgG) |
| | 1.0% | Pluronice<< F68 | d) Set of compartments C: Bp(f)2 (namely Ab-M): Elutable conjugate consisting of a polyclonal anti-body directed against T3 and peroxidase (PAB<T3>-POD).

| Coating solution: | 22.2 U/ml | PAB<T3>-POD |
|---|---|---|
| | 120 mM | sodium barbiturate |
| | 21.8 mM | NaPB pH 8.35 |
| | 0.04% | ANS |
| | 0.02% | 4-aminoantipyrine |
| | 0.01% | Merthiolate |
| | 0.25 | B-IGG |
| | 1.0% | Pluronice<< F68 |

Test strips of 3.2 mm in height and 15 mm in length were cut out of the coated polystyrene film, the compartments running over their entire height perpendicularly to the longitudinal direction. The total molar amounts of reagent present in such a test strip in the particular compartments were:

In the set of compartments C: 0.05 femtomol of PAB<T3>-POD (=1.4 μU)

In the set of compartments B: 23.0 femtomol of T3-biotin

In the set of compartments A: ca. 500.0 femtomol of biotin binding sites (through TBSA-SA)

A T3 analysis was carried out as follows:

50 μl of each T3-containing sample were applied to a test strip and incubation was carried out for 2.5 h at room temperature in a humidity chamber.

The test strip was washed 4 times with 1 ml of the BSA solution used for the protective layer.

A substrate for the labelling enzyme, namely 50 μl of diaminobenzidine (DAB) colour reagent (0.5 mg/ml of DAB, 40 mM NaPB pH 7.4, 0.025% of cobalt chloride, 0.02% of nickel sulphate, 0.01% of hydrogen peroxide), was applied and incubation was carried out for one hour at room temperature in the humidity chamber.

The strip was then washed with water.

The test is based on the competitive principle explained above: the T3 competes with the biotinylated T3 for binding sites on the PAB<T3>-POD conjugate.

A visually recognizable colouration of the set of compartments A, of varying intensity, was produced as a function of the T3 concentration in the sample. Determination of the pattern of compartments by a measurement technique permits calibration and quantitative evaluation.

EXAMPLE 2

Construction and manufacturing process corresponding to Example 1 with the exception of the composition of the solutions used for the sets of compartments B and C. These had the following compositions:

a) Set of compartments B: Bp(f)1 (namely B-Ab): Elutable conjugate consisting of a monoclonal antibody directed against TSH (ECACC 87122201) and biotin (MAB<TSH>-biotin). The biotinylation of the antibody was carried out according to JACS 100 (1978, 3585–3590) by reaction with N-hydroxysuccinimidobiotin in a ratio of 10:1.

| Coating solution: | 80 Mm | NaPB pH 7.4 |
|---|---|---|
| | 65 μg/ml | MAB<TSH>-biotin |
| | 0.6% | BSA |
| | 0.3% | bovine IgG | b) Set of compartments C: Bp(f)2 (namely Ab-E): Elutable conjugate consisting of peroxidase and a monoclonal antibody directed against TSH (ECACC 87122202) (MAB<TSH>-POD).

| Coating solution: | 50 mM | NaPB pH 7.4 |
|---|---|---|
| | 9 U/ml | MAB<TSH>-POD |

The test procedure corresponds to the heterogeneous one-step sandwich test with streptavidin-biotin capturing system for binding of the immunological complex to the fixed phase.

Test strips were again prepared with the same dimensions as in Example 1. Each test strip comprises 18 compartments of set A and 9 compartments each of sets B and C.

The analysis was performed as in Example 1, except that in the first step 100 μl of each TSH-containing sample were applied and incubation was carried out for 3 h at RT in a humidity chamber.

As in Example 1, a visually clearly recognizable colouration, of varying intensity, of the compartments of set A was produced.

We claim:

1. An analysis element for bioreactively analyzing a liquid sample, said analysis element comprising:

a carrier layer having a plurality of sets of compartments thereupon, each of said compartments comprising a reagent applied in a predetermined pattern by an ink-jet process, the compartments of a first set being fixed compartments containing a first binding partner which is solid phase bound to the carrier layer, and which is capable of binding specifically to a corresponding binding partner which is contained in the liquid sample or in a second set of compartments, said fixed compartments containing the first binding partner being covered by a layer of an inert water soluble protein substance, with compartments of at least one set being elutable compartments containing a labelled second binding partner which is elutable and which is disposed adjacent to a top surface of the layer of inert water soluble protein substance, said labelled second binding partner being capable of binding bioreactively and specifically to a corresponding binding partner contained in the liquid sample or another set of compartments, wherein the layer of inert water soluble protein substance is located between the carrier layer and the elutable compartments containing the labelled second binding partner, and over the fixed compartments, wherein the layer of inert water soluble protein substance forms a continuous layer which spatially separates said fixed compartments and said elutable compartments, wherein said fixed compartments and said elutable compartments are arranged in an alternating horizontal relationship with the layer of inert water soluble protein substance therebetween.

2. The analysis element of claim 1, wherein the first binding partner is bound to the carrier layer in a concentration which is lower than a binding capacity of the carrier layer.

3. The analysis element of claim 1, wherein a third binding partner is contained in a third set of compartments, said third set of compartments being disposed adjacent to said second set of compartments, wherein the third binding partner is a conjugate which comprises a first component with binding affinity for said first binding partner and a second component with binding affinity for either said second binding partner or a corresponding binding partner in the liquid sample.

4. The analysis element of claim 3, wherein the first binding partner comprises avidin or streptavidin and the first component of the third binding partner is biotin.

5. The analysis element of claim 3, wherein the first binding partner and the third binding partner form a capturing system.

6. The analysis element of claim 1, wherein said carrier layer is a plastic layer.

7. A process for manufacturing an analysis element for bioreactively analyzing a liquid sample, said process comprising the steps of:

providing a carrier layer;

applying a plurality of discrete quantities of a liquid reagent comprising a first binding partner to form separate compartments on said carrier layer by ejecting the liquid reagent in discrete droplet form from an ink-jet head onto a reagent domain portion of the carrier layer;

applying a layer of inert water soluble protein substance to said reagent domain portion of the carrier layer, thereby covering said discrete quantities of liquid reagents and portions of said carrier layer with no applied liquid reagent; and applying a labelled second binding partner id discrete droplet form from an ink-jet head upon selected portions of said layer of inert water soluble protein substance;

wherein the ink-jet head and carrier layer are moved relative to each other during said applying steps in a predetermined pattern so that the dots produced on the carrier layer by the droplets form a plurality of the compartments on the reagent domain portion, with the compartments of a first set being fixed compartments containing the first binding partner which is solid phase bound to said carrier layer, and which is capable of binding specifically to a second binding partner in said liquid sample or in said second set of compartments, with compartments of at least one second set being elutable compartments containing the second binding partner which is disposed adjacent to a top surface of the layer of inert water soluble protein substance, said second binding partner being elutable and which is capable of binding specifically to a corresponding binding partner contained in the liquid sample or the first set of compartments, and wherein the layer of inert water soluble protein substance is located between the carrier layer and the elutable compartments containing the second binding partner, and over the fixed compartments which forms a continuous layer that spatially separates said fixed compartments from said elutable compartments, with the fixed compartments and the elutable compartments being arranged in an alternating horizontal relationship with the layer of inert water soluble protein substance therebetween.

8. The process of claim 7, wherein the carrier layer is a plastic layer, and including the further step of irradiating the plastic layer with gamma rays prior to application of the liquid reagents.

9. The process of claim 7, wherein the droplets of one of said liquid reagents are ejected to form a series of spatially separated first dots on the reagent domain as said separate compartments, and wherein a plurality of droplets are subsequently ejected to form dots on the spaces between the first dots, thereby forming a continuous compartment.

10. The process of claim 7, wherein a plurality of compartments of different sets are simultaneously produced by ejection of liquid reagents from a multichannel jet head.

11. The process of claim 7, wherein a volume of each droplet is 20 to 2000 picoliters.

* * * * *